United States Patent
Banerjee et al.

(10) Patent No.: US 6,333,433 B1
(45) Date of Patent: Dec. 25, 2001

(54) PROCESS FOR SYNTHESIS OF NOVEL CATIONIC AMPHIPHILES CONTAINING N-HYDROXYALKL GROUP FOR INTRACELLULAR DELIVERY OF BIOLOGICALLY ACTIVE MOLECULES

(75) Inventors: Rajkumar Banerjee; Prasanta Kumar Das; Gollapudi Venkata Srilakshmi; Nalam Madhusudhana Rao; Arabinda Chaudhuri, all of Hyderabad (IN)

(73) Assignee: Council of Scientific Industrial Research, New Delhi (IN)

( * ) Notice: Subject to any disclaimer, the term of this patent is extended or adjusted under 35 U.S.C. 154(b) by 0 days.

(21) Appl. No.: 09/275,816

(22) Filed: Mar. 25, 1999

(30) Foreign Application Priority Data

Nov. 9, 1998  (IN) .............................. 3325/DEL/98
Nov. 9, 1998  (IN) .............................. 3327/DEL/98
Nov. 9, 1998  (IN) .............................. 3324/DEL/98

(51) Int. Cl.[7] .................................. C07C 209/00
(52) U.S. Cl. ............................ 564/296; 564/292
(58) Field of Search ............... 554/149; 564/296, 564/292

(56) References Cited

FOREIGN PATENT DOCUMENTS

97/38968 * 10/1999 (WO).

OTHER PUBLICATIONS

Hayashi et al, Preparation of tertiary amines having different substituents from quaternary 2–hydroxyethylammonium salts, AN 1988:74771 CAPLUS.*

Sheibel, Preparation of alkul substituted tertiary amine feedstocks for surfactants, see abs, AN 1997:696735.*

Hashimoto et al, Lubricating oil aDditives and lubricating oil compositions, see abs, AN 1997:650422.*

* cited by examiner

Primary Examiner—Deborah D. Carr
(74) Attorney, Agent, or Firm—Finnegan, Henderson, Farabow, Garrett & Dunner, L.L.P.

(57) ABSTRACT

The present invention provides processes for the synthesis of novel cationic amphiphiles capable of facilitating transport of biologically active molecules into cells wherein the said amphiphiles contain N-hydroxyalkyl group and have at least one hydroxyalkyl group containing 1–3 carbon atoms directly linked to the positively charged nitrogen atom.

14 Claims, 7 Drawing Sheets

Figure 1:
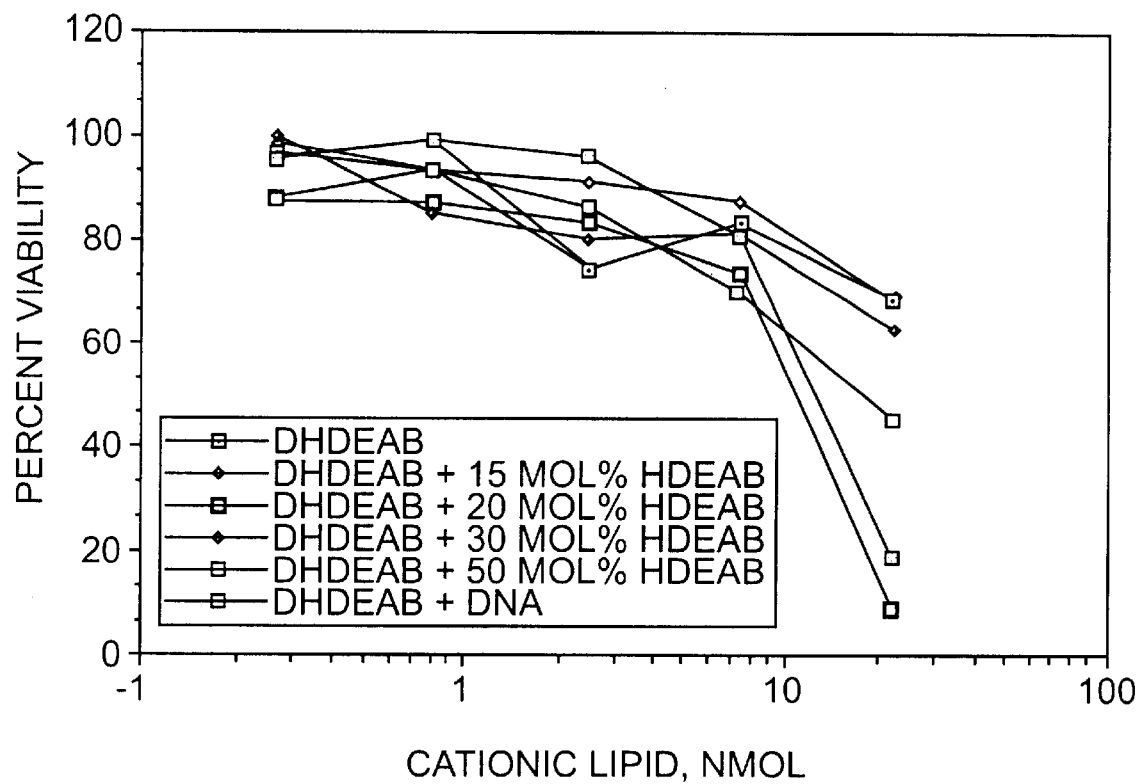

PROCESS FOR SYNTHESIS OF NOVEL CATIONIC AMPHIPHILES CONTAINING N-HYDROXYALKL GROUP FOR INTRACELLULAR DELIVERY OF BIOLOGICALLY ACTIVE MOLECULES

FIELD OF THE INVENTION

The present invention relates to processes for preparing novel cationic amphiphiles containing N-hydroxyalkyl group. The invention provides novel compositions containing the said amphiphiles that are useful to facilitate transport of biologically active molecules into cells. The area of medical science that is likely to benefit most from the present invention is gene therapy.

BACKGROUND

In gene therapy, patients carrying identified defective genes are supplemented with the copies of the corresponding normal genes. However, genes (DNA), the polyanionic macromolecules and the cell surfaces of the biological membranes both being negatively charged, spontaneous entry of normal copies of genes into the target cells of patients is an inefficient process (because of electrostatic repulsion). This is why the past decade has witnessed an unprecedented upsurge of global interest in developing efficient gene delivery reagents for introducing normal genes into the target cells of patients suffering from various genetic (inherited) diseases such as cystic fibrosis, Gaucher's illness, Fabry's disease etc. Many gene delivery reagents (also known as transfection vectors) including retrovirus, adenovirus, and cationic amphiphilic compounds (i.e. compounds containing both polar and non-polar functionalities) are being used as the carriers of polyanionic genes in combating hereditary diseases in gene therapy. The amphiphilic nature (presence of both polar and non-polar regions in the molecular structures) of the compounds designed to deliver therapeutically actives molecules, ensures smooth interaction of these carrier molecules with the polar and non-polar regions of plasma membranes, compartments within the cells and the biologically active molecules itself. At physiological pH, the cationic amphiphiles in the form of liposomes or micelles associate favorably with the negatively charged regions of the macromolecular polyanionic DNA enhancing the intracellular uptake of the resulting complex between the cationic lipids and the negatively charged DNA. Reproducibility, high degree of targetability and low cellular toxicity are increasingly making the cationic amphiphiles the transfection vectors of choice in gene therapy.

PRIOR ART REFERENCES

An impressive number of cationic lipids with varying structures have been reported for the intracellular delivery of therapeutically active molecules as exemplified by the following references:

Felgner et al., *Proc. Natl. Acad. Sci. U.S.A.*, 84, 7413–7417 (1987), reported the first use of a highly efficient cationic lipid N-[1-(2,3-dioleyloxy)propyl]-N,N,N-trimethyl ammonium chloride (DOTMA) as the DNA transfection vector.

U.S. Pat. Nos. 4,897,355 and 4,946,787 (1990) reported the synthesis and use of N-[.omega..(.omega.-1)dialkyloxy]- and N-[..omega..(.omega.-1)-dialkenyloxy]-alk-1-yl-N,N,N-tetrasubstituted ammonium amphiphiles and their pharmaceutical formulations as efficient transfection vectors.

Leventis, R. and Silvius, J. R. *Biochim. Biophys. Acta* 1023, 124–132, (1990) reported the interactions of mammalian cells with lipid dispersions containing novel metabolizable cationic amphiphiles.

U.S. Pat. No. 5,264,618 (1993) reported the synthesis and use of additional series of highly efficient cationic lipids for intracellular delivery of biologically active molecules.

Felgner et al. *J. Biol. Chem.* 269, 2550–2561 (1994) reported enhanced gene delivery and mechanistic studies with a novel series of cationic lipid formulations.

U.S. Pat. No. 5,283,185 (1994) reported the synthesis and use of 3β[N-(N$^1$,N$^1$-dimethylaminoethane)carbamoyl] cholesterol, termed as "DC-Chol" for delivery of a plasmid carrying a gene for chloraniphenicol acetyl transferase into cultured mammalian cells.

U.S. Pat. No. 5,283,185 (1994) reported the use of N-[2-[[2,5-bis[(3-aminopropyl)amino]-1-Oxopentyl] aminoethyl]-N,N-dimethyl-2,3-bis-(9 -Octadecenyloxy)-1-Propanaminium tetra (trifluoroacetate), one of the most widely used cationic lipids in gene delivery. The pharmaceutical formulation containing this cationic lipid is sold commercially under the trade name "Lipofectamine".

Solodin et al. *Biochemistry* 34, 13537–13544, (1995) reported a novel series of amphiphilic imidazolinium compounds for in vitro and in vivo gene delivery.

Wheeler et al. *Proc. Natl. Acad.Sci. U.S.A.* 93, 11454–11459, (1996) reported a novel cationic lipid that greatly enhances plasmid DNA delivery and expression in mouse lung.

U.S. Pat. No. 5,527,928 (1996) reported the synthesis and the use of N,N,N,N-tetramethyl-N,N-bis(hydroxy ethyl)-2,3-di(oleolyoxy)-1,4-butanediammonium iodide i.e. pharmaceutical formulation as transfection vector.

7 U.S. Pat. No. 5,698,721 (1997) reported the synthesis and use of alkyl O-phosphate esters of diacylphosphate compounds such as phosphatidylcholine or phosphatidylethanolamine for intracellular delivery of macromolecules.

U.S. Pat. Nos. 5,661,018; 5,686,620 and 5,688,958 (1997) disclosed a novel class of cationic phospholipids containing phosphotriester derivatives of phosphoglycerides and sphingolipids efficient in the lipofection of nucleic acids.

U.S. Pat. No. 5,614,503 (1997) reported the synthesis and use of an amphipathic transporter for delivery of nucleic acid into cells, comprising an essentially nontoxic, biodegradable cationic compound having a cationic polyamine head group capable of binding a nucleic acid and a cholesterol lipid tail capable of associating with a cellular membrane.

U.S. Pat. No. 5,705,693 (1998) disclosed the method of preparation and use of new cationic lipids and intermediates in their synthesis that are usefull for trasfecting nucleic acids or peptides into prokaryotic or eukaryotic cells. These lipids comprise one or two substituted arginine, lysine or ornithine residues, or derivatives thereof, linked to a lipophilic moiety.

U.S. Pat. No. 5,719,131 (1998) has reported the synthesis of a series of novel cationic amphiphiles that facilitate transport of genes into cells. The amphiphiles contain lipophilic groups derived from steroids, from mono or dialkylamines, alkylamines or polyalkylamines.

Although the above mentioned cationic lipids have been successfully exploited for the intracellular delivery of genes, the efficiencies for the intracellular uptake procedures are insufficient and need to be improved. The transfection activities of most of the above mentioned cationic lipids are modest and therefore substantial quantities of these cationic lipids must be consumed. The associated cellular toxicities of the lipids and the metabolites thereof are, thus naturally, issues of concern. Accordingly, demands for developing new class of cationic amphiphiles with high transfection efficiencies and low cellular toxicities continue in this field of art.

OBJECTS OF THE INVENTION

The main objective of the present invention is to provide novel simple and economic processes for the synthesis of cationic amphiphilic compounds containing non-toxic N-hydroyalkyl group.

Another objective of the invention is to provide processes for the synthesis of said novel cationic amphiphilic compounds which are useful for delivery of therapeutically effective amounts of biologically active molecules into cells/tissues of patients.

Yet another objective of the invention is to provide novel processes for the synthesis of cationic amphiphilic compounds such that a hydrophobic group is either directly linked to the positively charged Nitrogen atom or is linked to the said Nitrogen atom via an ester or methylene group.

Still another objective of the invention is to provide novel processes for the synthesis of cationic amphiphilic compounds with at least one hydroxyalkyl group containing 1–3 carbon atoms directly linked to the positively charged Nitrogen atom.

Yet another objective of the invention is to provide novel cationic amphiphilic compounds without any glycerol backbone in their structure.

DETAILED DESCRIPTION OF THE INVENTION

The present invention relates to novel cationic amphiphiles containing non-toxic N-hydroxyalkyl group and provides processes for the preparation said amphiphilic compounds. The novel cationic amphiphiles containing N-hydroxyalkyl group of this invention are potentially useful to deliver into the cells of patients therapeutically effective amounts of biologically active molecules. The area of medical science that is likely to benefit most from the present invention is gene therapy.

Cationic amphiphiles disclosed in the present invention possess several novel structural features. These features may be compared with cationic amphiphilic structures disclosed in Felgner et al. *J. Biol. Chem.*, 269, 2550–2561 (1994), a representative structure of which is 1,2-dimyristyloxypropyl-3-dimethyl-hydroxyethyl ammonium bromide ("DMRIE") and to those disclosed by Bennett et al. *J. Med. Chem.*, 40, 4069–4078 (1997), a representative structure of which is N,N-[Bis(2-hydroxyethyl)]-N-methyl-N-[2,3-bis(tetradecanoyloxy)propyl] ammonium chloride ("DMDBP").

The following distinctive structural features are common to the cationic amphiphiles disclosed in the present invention: (1) the presence of a hydrophobic group which is either directly linked to the positively charged nitrogen atom or is linked to the positively charged nitrogen via an ester group, (2) the presence of at least one hydroxyalkyl group containing 1–3 carbon atom that is directly linked to the positively charged nitrogen atom and (3) unlike many other glycerol-based cationic amphiphiles, the cationic transfection lipids disclosed in the present invention do not have any glycerol backbone in their molecular architecture. It is believed that these unique structural features contribute significantly to the increased transfection efficiencies of the cationic amphiphiles disclosed herein. The enhanced in vitro transfection efficiencies of N,N,-di-[O-hexadecanoyl] hydroxyethyl-N-hydroxyethyl-N-methylammonium bromide (DOHEMAB) and N,N-di-n-hexadecyl-N,N-dihydroxyethylammonium bromide (DHDEAB), the two novel transfection lipids of the present invention, is compared to Lipofectamine, the most widely used commercially available highly efficient transfection lipid.

According to the practice of the present invention, "cationic" means the positive charge is either on a quaternized nitrogen atom or on a protonated tertiary nitrogen atom. The cationic characters of the amphiphiles may contribute to the enhanced interaction of the amphiphiles with biologically active molecules (such as nucleic acids) and/or with cell constituents such as plasma membrane glycoproteins. Such enhanced interaction between the cationic transfection lipid and the biological by active molecules and/or cell membrane constituents may play a key role in successfully transporting the therapeutic molecules into the cells.

The cationic amphiphiles of the present invention have certain common structural and functional groups. As such, the said cationic amphiphilic compounds may be represented by the following generic formula:

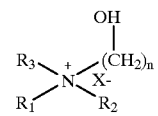

Wherein
n is an integer between 1 and 3,
$R_1$ may be H, saturated or unsaturated aliphatic group ($C_8$–$C_{20}$) or long chain saturated or unsaturated alkyl group ($C_7$–$C_{19}$).
$R_3$ may be hydroxyalkyl group of 1–3 carbon atoms,
$R_2$ may be a long chain saturated alkyl group ($C_7$–$C_{19}$) or $[(CH_2)_n\text{-}Z\text{-}R_2]$
Z may be methylene group (—$CH_2$), or an esteric group (—O—CO—)

Various novel amphiphilic compounds having the above basic structural formula are described in co-pending U.S. patent application Ser. No. .......... (Indian Application No.3324/DEL/98,3325/DEL/98 and 3327/DEL98 all dated Nov. 9, 1998). Further, in the said amphiphiles the preference of $C_8$–$C_{20}$ is specifically low because below the chain length of $C_8$ the amphiphiles loose the aggregation property and the specific reason for not using carbon chains longer than $C_{20}$ is because they are not compatible with biological membranes in terms of their lengths. Further, the additional linking groups that may be practised within the scope of this invention include —O—(ether) CONH-amide) group etc. Among the three different linking groups described in the invention herein below, the esteric group is most prefeiri Further, the products obtained during the synthesis of the said amphiphilic compounds are hydrolysis products. The molecules were so constructed to aid in their breakdown within a cell subsequent to performing the task of transfection. The structure of the amphiphiles may also be altered by a combination of alkyl and amine moieties, which structures would fall within the teachings and scope of the present invention. Such modifications are apparent to those skilled in the art.

Accordingly, the invention provides cationic amphiphiles represented by the following structural formula (I):

(I)

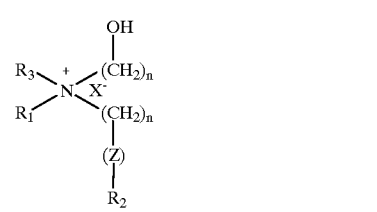

Wherein:

n is an integer between 1 and 3;

R₁ represents either H or a saturated aliphatic group;

R₂ independently represents a long chain saturated alkyl group (from $C_7$ to $C_{19}$);

R₃ is a small hydroxyalkyl group containing 1–3 carbon atoms;

X is either a halogen atom or a tosylate group.

Z represents a methylene (—CH₂—) group;

The process for the synthesis of said cationic amphiphilic compounds having the above structural formula (I) comprises reacting the secondary amine containing the N-hydroxyalkyl group such as diethanolamine with a saturated alkyl halides or saturated alkyl tosylates in a polar solvent in the presence of a weak tertiary base.

In an embodiment of the invention, the N-hydroxyalkyl group may be diethanolarnine.

In another embodiment, the saturated alkyl bromides employed in the process may be selected from the group consisting of n-hexadecyl bromide.

In yet another embodiment, the polar solvents in which the reaction may be carried out may be selected from the group comprising alcohols, diemethyl formamide, dimethylacetamide, acetonitrile, methylisobutyl ketone.

In still another embodiment of the invention, the base may be selected from sodium or potassium carbonate.

In yet another embodiment, the reaction for the synthesis of said amphiphilic lipids may be carried out at a temperature in the range of 0°–250° C., preferably at the reflux temperature (boiling point of the solvent selected).

According to an aspect of the invention, a pair of particularly effective representative cationic amphiphiles that may be synthesised by the said reaction, would include N,N-di-n-hexadecyl-N,N-dihydroxyethylammonium bromide (DHDEAB), amphiphile No 1 and N-n-hexadecyl-N, N-dihydroxyethylammonium bromide (HDEAB), amphiphile No. 2 represented as under:

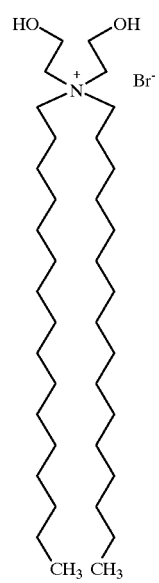

1

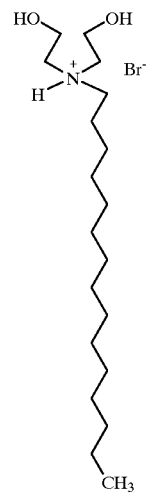

2

The process for the synthesis of said cationic lipids is schematically represented hereunder.

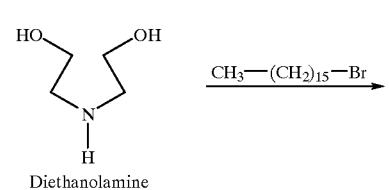

Diethanolamine

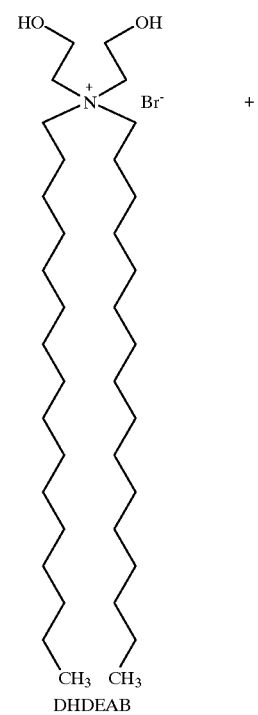

DHDEAB

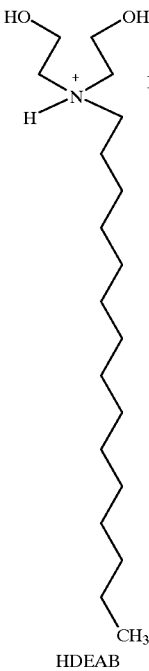

HDEAB

The invention further provides cationic amphiphilic compounds represented by the structural formula (II):

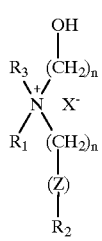

(II)

wherein:
n is an integer between 1 and 3;
$R_1$ independently, represents either a saturated aliphatic group or an unsaturated aliphatic group (from $C_8$ to $C_{20}$);
Z represents a methylene (—$CH_2$—) group;
$R_2$, independently, represents a long-chain saturated alkyl group (from $C_7$ to $C_{19}$);
$R_3$ is a small alkyl group (from $C_1$ to $C_3$);
X is either a halogen atom or a tosylate group.

The process for the synthesis of said cationic amphiphilic compounds having the above structural formula, comprises:
(a) coupling the aliphatic unsaturated aldehyde with the alkyl amine followed by the reduction of the resulting imine to obtain the corresponding secondary amine;
(b) reacting the secondary amine obtained in step (a) with the hydroxyl-protected hydroxyalkyl halide followed by removal of the hydroxyl protecting group to obtain the corresponding N-hydroxyalkyl group containing tertiary amine and
(c) quaternizing the resulting N-hydroxyalkyl group containing tertiary amine obtained in step (b) with an alkyl halide or alkyl tosylates in a mixed polar solvent.

In an embodiment of the invention, the saturated or unsaturated aldehyde used may be oleyl aldehyde.

In another embodiment, the alkyl amine used may be n-octadecyl amine.

In yet another embodiment, the tertiary amine may be quarternized with alkyl iodide selected from methyl iodide.

In yet another embodiment, the mixed polar solvent may comprise a mixture of methanol and chloroform.

In yet another embodiment, the resultant tertiary amine of step (b) may be N-hydroxyethyl-N- oleyl-N-n-octadecyl-amine In an embodiment, the reaction of amine with the aldehyde in step (a) is generally performed in a dry chlorinated solvent such as dichloromethane with temperature in the range of –78° C. to 10° C. and the reduction of the resulting intermediate imine is carried out with sodium borohydride in a mixed polar solvent such as methanol and dichloromethane with temperature in the range of –5° C. to 40° C. The step (b) is generally carried out in a polar solvent such as ethyl acetate, N,N-dimethyl formamide, acetonitrile and the like in the presence of a weak base such as sodium or potassium carbonate. The solvent selected in removing the hydroxyl protecting group in step (b) is generally polar aprotic in nature such as tetrahydrofuran, dimethyl formamide and the like. The final quarternization in step (c) is carried out using the appropriate alkyl polar solvent such as methanol and chloroform at a temperature in the range –5° C. to 40° C.

According to this aspect of the invention, a particularly effective representative pair of cationic transfection lipids prepared by the above process would include, for example, N-methyl-N-n-octadecyl-N-oleyl-N-hydroxyethyl-ammonium chloride (MOOHAC), amphiphile No 3 and NN-di-n-octadecyl-N-methyl-N-dihydroxyethylammonium chloride (DOMBAC), amphiphile No. 4, whose structural formulae are represented hereunder:

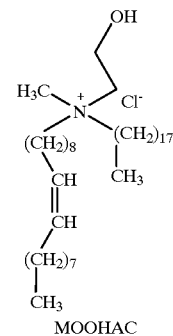

MOOHAC

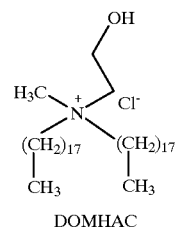

DOMHAC

A schematic representation of the process described above for the synthesis of said cationic amphiphiles is provided hereunder for reference:

Scheme II
Synthesis of MOOHAC & DOMHAC

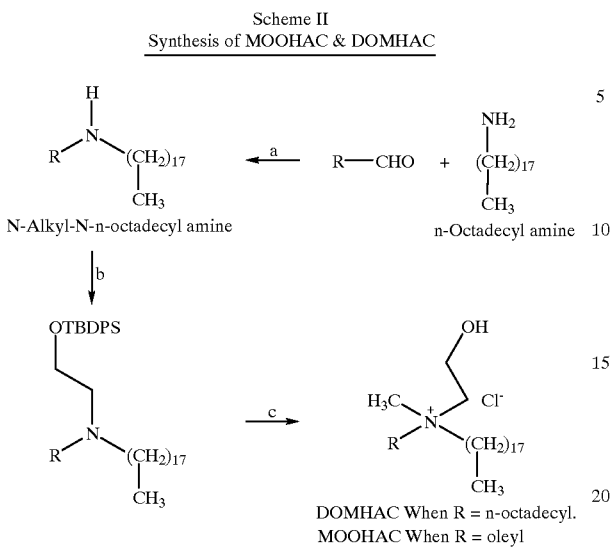

The invention further provides a process for the preparation of cationic amphiphiles represented by the structural formula (mH) given hereunder:

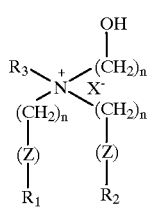

(III)

wherein:

n is an integer between 1 and 3, Z an ester group (—O—CO—) and $R_1$ and $R_2$ independently, represent a long-chain saturated or unsaturated alkyl group (from $C_7$ to $C_{19}$), $R_3$ is a small alkyl group ($C_1$ to $C_3$) and X is either a halogen atom or a tosylate group.

The process for the synthesis of said cationic amphiphilic compounds, comprises:

(a) reacting an acid chloride with a tertiary amine containing the N,N-dihydroxyalkyl group to obtain the hydrochloride salt of the corresponding di-Oacylated product, (b) neutralizing the resulting hydrochloride salt obtained in step (a) with alkali and (c) quaternizing the resulting tertiary amine obtained in step (b) with the appropriate hydroxy-alkyl halide.

In an embodiment of the invention, the acid chloride used in step (a) may be n-hexadecanoyl chloride.

In another embodiment, the tertiary amine in step (a) may be N-methyldiethanolamine.

In yet another embodiment, the reaction in step (a) may be performed at a temperature in the range of 10°–50° C., in a polar aprotic solvent selected from the group comprising N,N-dimethylformamide, acetonitrile and the like.

In yet another embodiment, the neutralization in step (b) may be carried out in a biphasic solvent such as mixture of dichloromethane and water or ethyl acetate and water using strong alkali such as NaOH or KOH.

In yet another embodiment, the quarternization in step (c) is carried out at a temperature in the range of 40° C. to 100° C. depending on the nature of alkyl halides used.

In another embodiment, the hydroxyalkyl halide used in step (a) is 2-bromoethanol.

According to this aspect of the invention, a particularly effective cationic transfection lipid that may be prepared by the above process includes-N,N,-di[O-hexadecanoyl] hydroxyethyl-N-hydroxyethyl-N-methylammonium bromide (DOHEMAB), amphiphile 5 having the structural formula as hereunder:

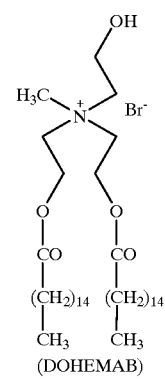

The said process taught for the synthesis of cationic lipids is schematically represented hereunder:

Scheme III

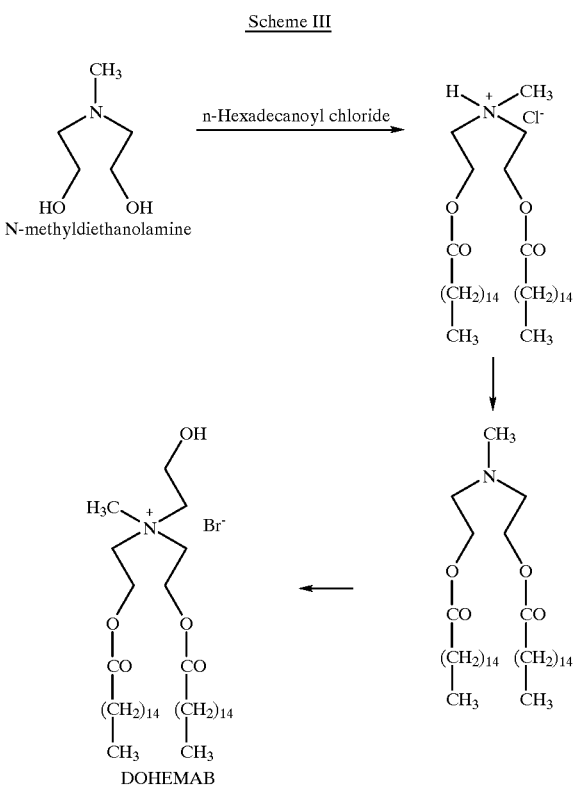

BRIEF DESCRIPTION OF THE ACCOMPANYING DRAWINGS

Figure 2:
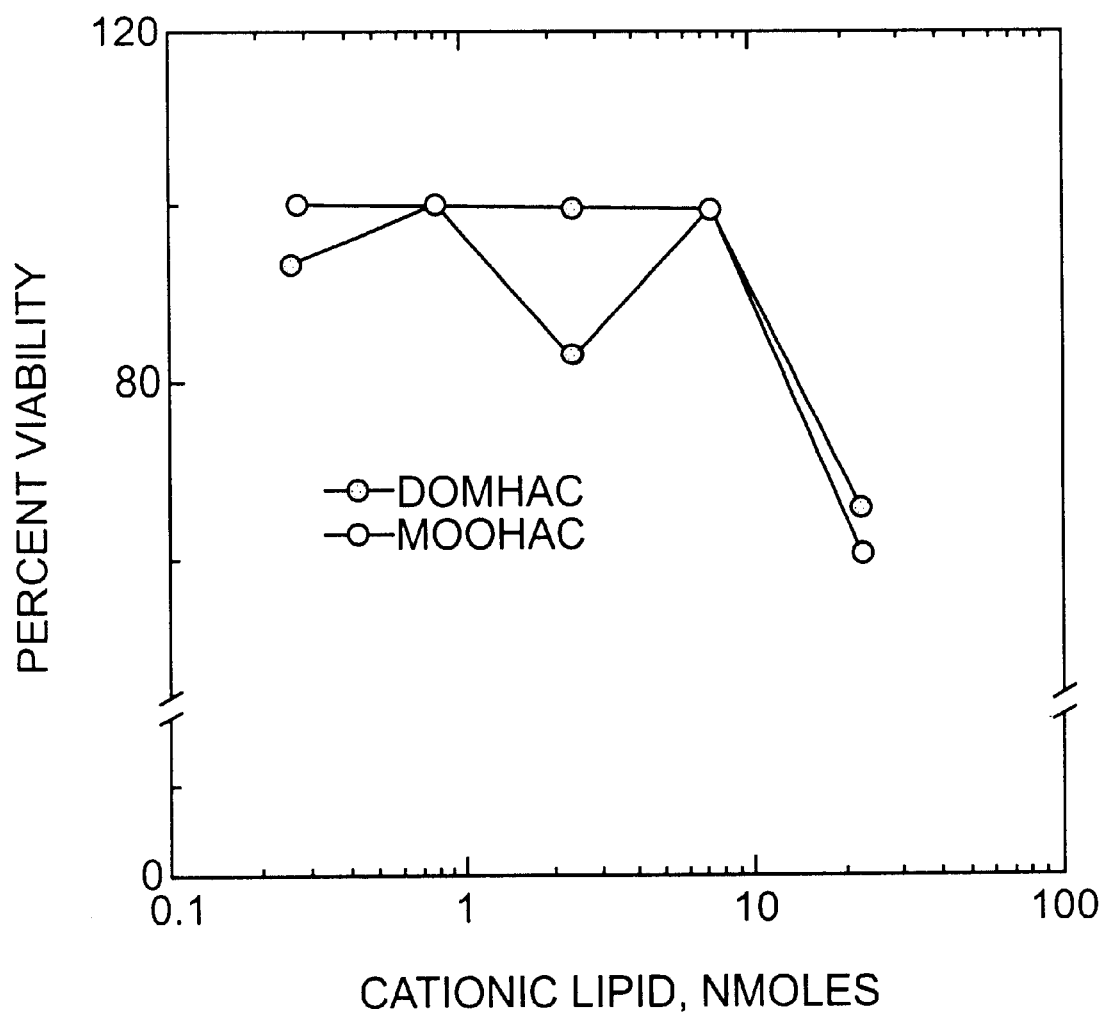

FIG. 1 and 2 provide the in vitro cellular toxicities of the cationic amphiphiles disclosed in the present invention.

FIGS. 3–7 provide in vitro transfection efficiencies for the cationic amphiphiles disclosed in the present invention and that of Lipofectamine, the most widely used commercially available transfection lipid, under certain conditions.

Figure 3:
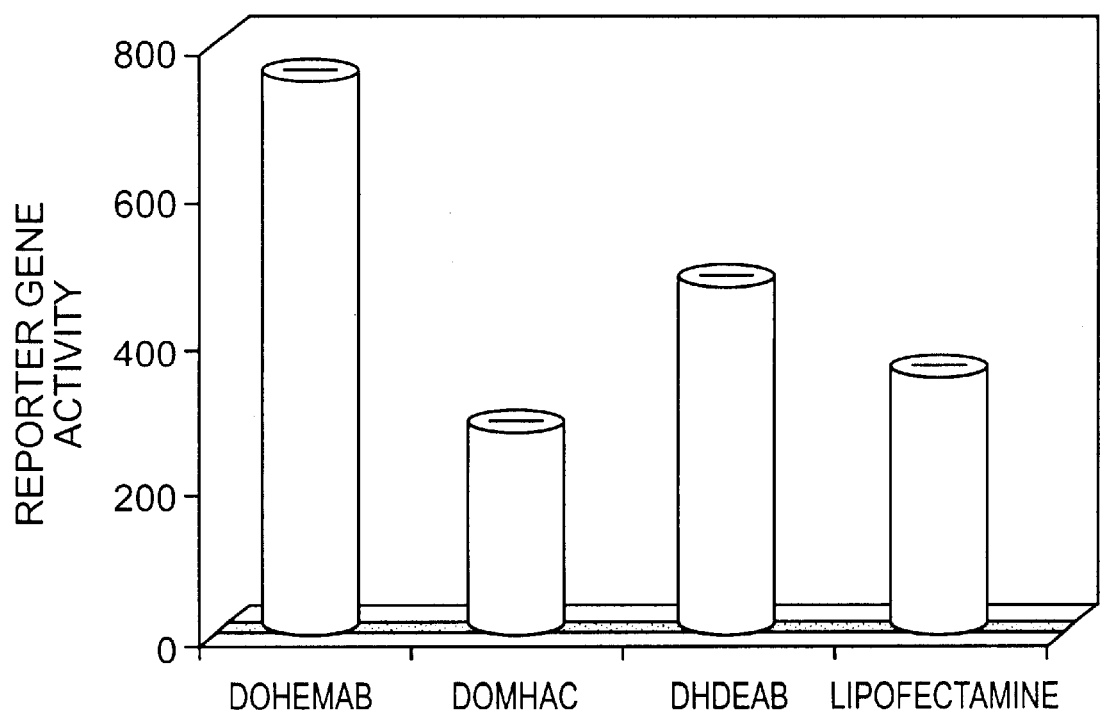

Formulations Containing the Cationic Amphiphiles of the Invention and the in vitro Administration Thereof The present invention provides for various formulations that facilitate intracellular delivery of biologically active molecules. The formulations of the transfection lipids disclosed herein were prepared either by keeping the amount of the cationic amphiphiles constant at 1 mM and varying the amounts of the auxiliary neutral lipid (cholesterol) within the range 0.2 mM to 1 mM or by adding varying amounts of the novel single-chain auxiliary cationic lipid N-n-hexadecyl-N,N-dihydroxyethylammonium bromide (HDEAB) within the range of 0.15 mM–0.5 mM to a mixture containing 1 mM of cholesterol and 1 mM twin-chain novel cationic amphiphiles disclosed herein. As shown in FIG. 3 of the drawings accompanying this specification, combination of 1 mM DHDEAB and 0.6 mM Cholesterol is a highly efficient formulation. Similarly, FIG. 4 of the drawings accompanying this specification shows an additional highly effective formulation containing 0.2 mM HDEAB, 1 mM DHEAB and 1 mM Cholesterol.

Cellular Toxicities of the Cationic Amphiphiles Disclosed in the Invention

The viabilities of cells in presence of various cationic amphiphiles disclosed herein were checked according to the standard protocol described in "Animal Cell Culture. 2nd Edition. Ed. I.R.L Press t, Oxford University Press (1997)". The transfection efficiencies of the cationic lipids were studied in the range of 0–10 nmole and within this limit, the cell toxicities were observed to be minimal and the cell viabilities were determined to be more than 80% as summarized in FIGS. 1 and 2. The cationic amphiphiles were used at a concentration of 1 mM together with 1 mM cholesterol as the neutral co-lipid.

Main Advantages of the Present Invention

1. The procedures for making these novel cationic amphiphiles being simple, the prices of this new transfection reagent should be remarkably lower than that of LIPO-FECTAMINE™ and LIPOFECTIN™

2. The transfection efficiency of the novel cationic amphiphiles are much better than that of LIPOFECTIN™ and comparable to or better than the transfection efficiencies of LIPOFECTAMINE™.

3. The cationic amphiphiles disclosed in the present invention have been tested positive for transfecting COS 1, Hela, Vero, CV 1 and NIH3T3 cells and the primary cell line, Rat Skin Fibroblasts.

The following examples are given by way of illustration of the present invention and therefore should not be construed to limit the scope of the present invention.

EXAMPLE 1

Cell Transfection Assay

Separate 1 $\mu$mole (80 $\mu$l of a 0.0126 M stock solution in chloroform) of N,N-di-n-hexadecyl-N,N-dihydroxyethylammonium bromide (DHEAB) and 1 $\mu$mole of the neutral colipid cholesterol (40 $\mu$l of a 0.0255 M stock solution in chloroform) were combined in a glass vial. The solvent was evaporated initially by a thin flow of moisture free nitrogen and then under high flow for two minutes and then further dried under vacuum (1 mm Hg) for 6 hours.

The dried lipid film was then hydrated with sterile deionized water (1 ml) overnight (9–10 hours) in room temperature to produce a dispersed suspension. The hydrated mixture was then vortexed for 1 minute and was sonicated in a probe sonicator at a constant 25 W sonic power for 5 minutes. The concentrations of both DHDEAB and cholesterol in the resulting solution obtained after sonication was 1 mM.

For preparation of the transfecting solution, DNA encoding $\beta$-galactosidase (pCH 110 construct as described in Borras et al. *Developmental Biology* 127, 209–219, 1988) was dissolved in DMEM culture medium (GIBCO/BRL No. 12800–017). The resulting solution had a DNA concentration of 454 $\mu$M (assuming an average molecular weight of 660 Dalton per base pair for nucleotides in the encoding DNA).

A 24 $\mu$l aliquot of the sonicated dispersion obtained (containing 1 mM of both cationic lipid and the colipid) was pipetted into separate wells of 96-well plate already containing 51 $\mu$l DMEM solution. The resulting 330 $\mu$M solution (with respect to both the cationic amphiphile and the colipid) was then three fold serially diluted for five times to obtain diluted amphiphile and cholesterol solutions within the range of 330 $\mu$M–4 $\mu$M, the volume of each resulting diluted solution being 50 $\mu$l. To each 50 $\mu$l resulting diluted solution, 2 $\mu$l of 454 $\mu$M DNA solution was added and the mixture was kept stirring for ½ hour at room temperature to allow for the DNA-lipid complexation.

A COS-1 (SV 40 transformed African green monkey kidney, # ATCCCRL 1650, from ATCL, Maryland, U.S.A.) cell line was used for the in vitro assay. The cells were cultured in DDEM media containing 10% fetal bovine serum ("FBS", Sigma F 0392) supplemented with Penicillin, Streptomycin and Kanamycin. Cells were plated into 24-well tissue culture plate to a density of approximately 5–6×10$^4$ cells/well and kept for about 12–14 hours until a near confluent (75–80%) pattern had been achieved.

To the DNA-lipid complex volume of 52 $\mu$l, 350 $\mu$l of DMEM was added and mixed thoroughly. The 24-well plates with COS-1 cells were aspirated in order to remove growth medium. The cells were washed once with phosphate buffered saline (PBS). Now to consecutive wells of 24-well plates, 201 $\mu$l of the DNA-lipid complex was added over the cells and the mixture was incubated for 3 hours in a $CO_2$ incubator. 200 $\mu$l of 10% FBS containing DMEM was added to each cell well. After a further 20 hour incubation period, the medium was removed and a fresh DMEM with 10% FBS was added. Following a further 24 hours incubation period, cells were assayed for expression of $\beta$-galactosidase and protein.

For protein estimation, the resultant medium was removed from the plates and the cells were were washed with PBS. Lysis buffer (100 $\mu$l containing 250 mM Tris.HCl, pH 8.0, 0.5% NP40) was added and the cells were lysed for 30 minutes. Lysate was passed through the pipette tip several times to dislodge and dissolve the cell fragments, 2.5 $\mu$l of lysate from each well was transferred to a 96-well plate containing 2.5 $\mu$l H$_2$O, 25 $\mu$l reagent A and 200 $\mu$l reagent B from the detergent compatible Bio-Rad protein assay kit (Bio-Rad 500-0116). The plates were read in an Elisa reader (Molecular Devices, Vmax) with a 650 nm filter. Proteins standard curve was also constructed by the same procedure using bovine serum albumin as standard.

The level of $\beta$-galactosidase activity in a 50 $\mu$l lysate was measured by adding to 50 $\mu$l of 2×$\beta$-gal mixture containing 1.33 mg/ml o-nitrophenyl-$\beta$-D-galactopyranoside (Sigma N1127), 200 mM sodium phosphate pH 7.15 and 200 mM magnesium sulfate. The o-nitrophenyl-$\beta$-D-galactopyranoside, following enzymatic hydrolysis at 37 °

Figure 4:
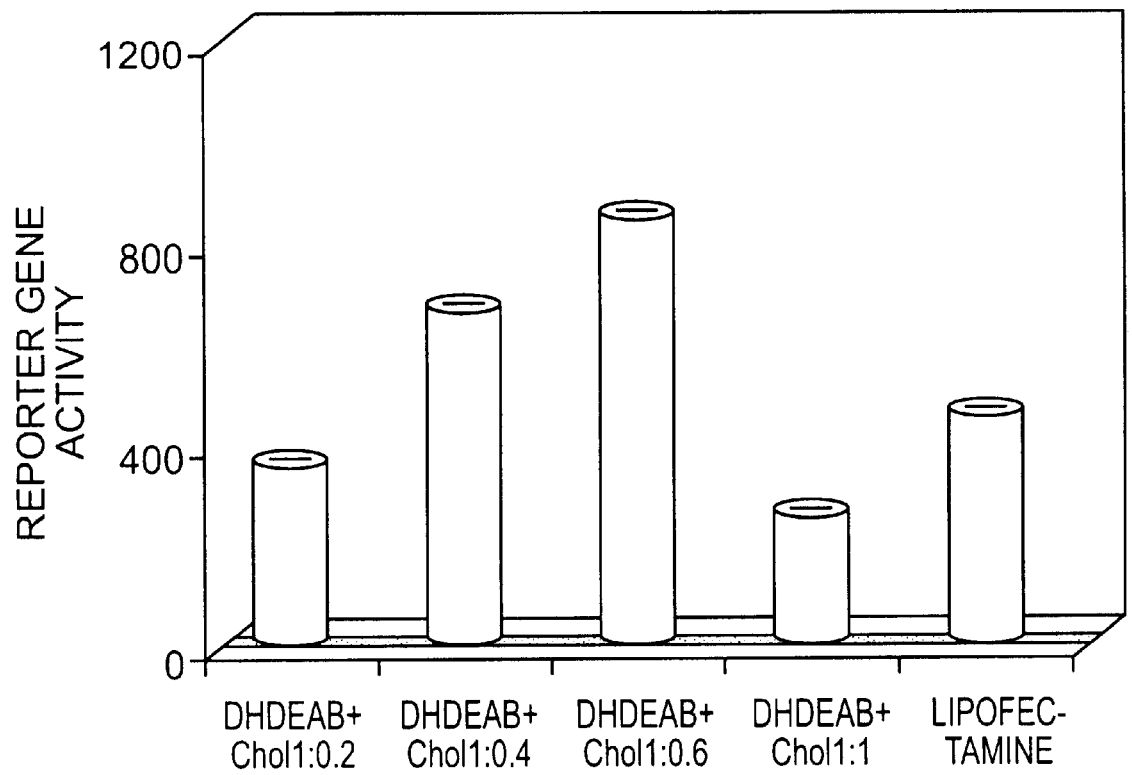
Figure 5:
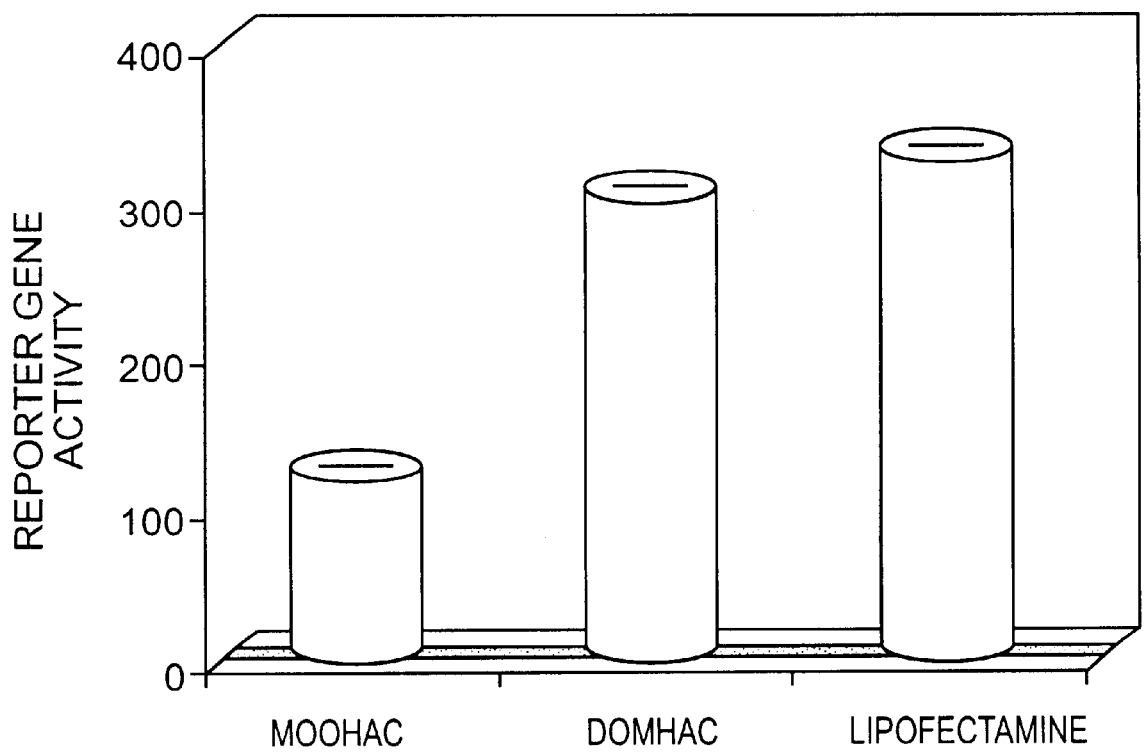
Figure 6:
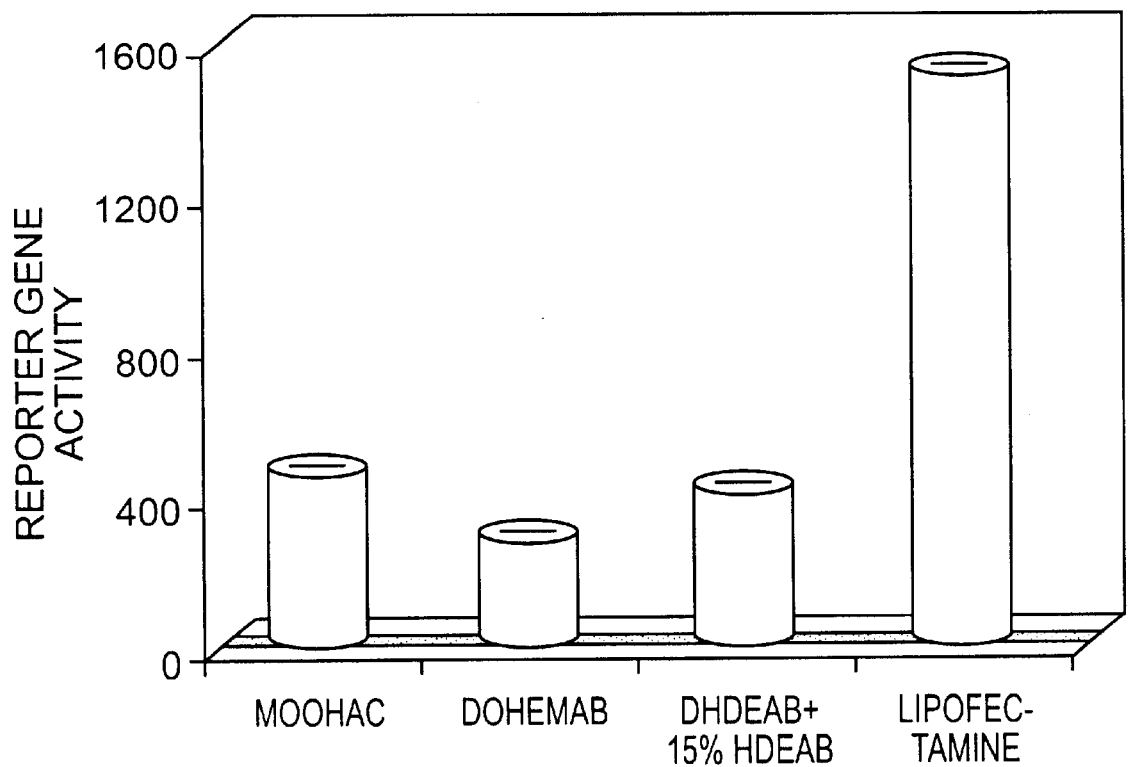
Figure 7:
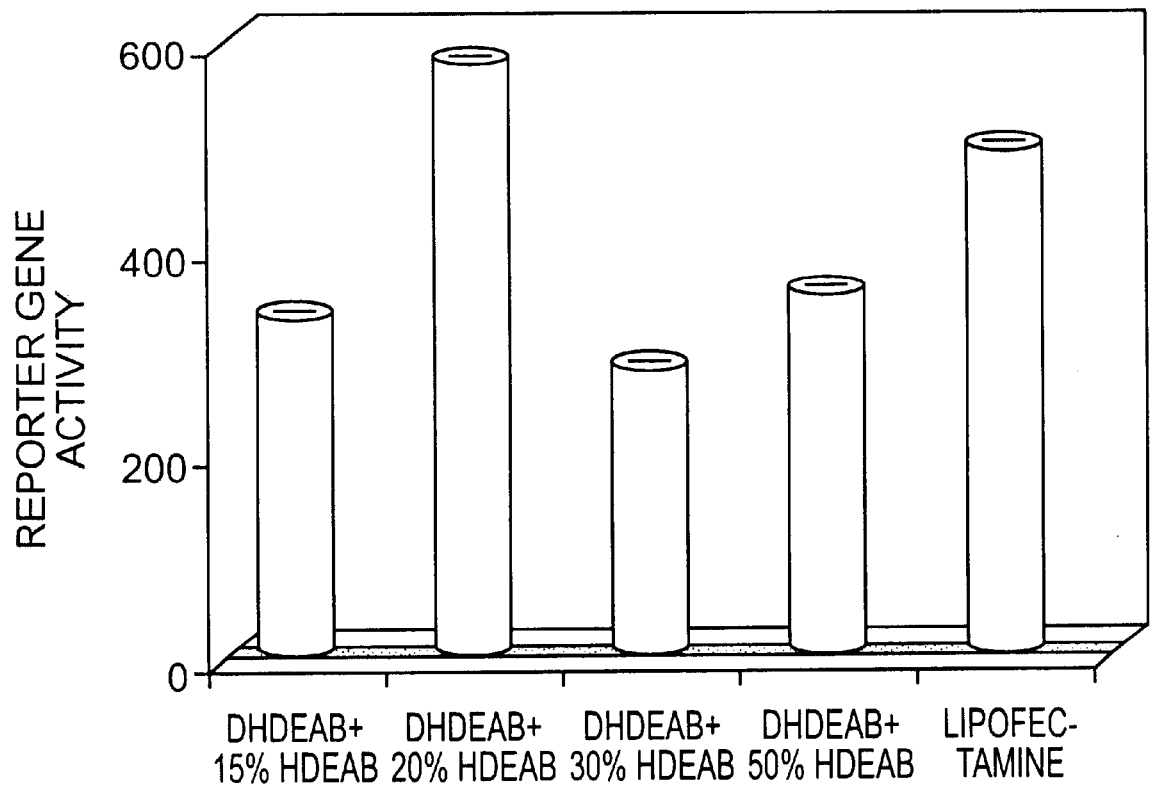

C. gave a yellow colour which was detected and measured by a plate reader equipped with a 405 mn filter. A β-galactosidase (Sigma No. G6512) standard calibration graph was constructed for calculating the amount of β-galactosidase in each well. Following subtraction of background readings, optical data determined by the plate reader allowed determination of β-galactosidase activity and protein content for each well. The results were finally summarized in terms of microunit of β-galactosidase per microgram of protein content (Reporter gene activity). Representative examples of such reporter gene activities observed with the cationic amphiphiles of the present invention are shown in FIGS. 2–4 of the drawings accompanying this specification.

The above described example is only an illustration with pCH 110. We have performed similar experiments with pCMV β-gal (GIBCO BRL, Gaithersberg, U.S.A.) & pGFPN1 (Clone Tech, Palo Alto, U.S.A.) and we have obtained similar reporter gene activities.

EXAMPLE 2

Procedure for the simultaneous preparation of N,N-di-n-hexadecyl-N,N-dihydroxyethylammonium bromide (DHDEAB), amphiphile No 1 and N-n-hexadecyl-NN-dihydroxyethylammonium bromide (HDEAB), amphiphile No. 2.

A mixture of diethanolamine (1 g, 9.5 mmol), n-hexadecyl bromide (2.9 g, 9.5 mmol) and potassium carbonate (1.44 g, 10.5 mmol) was Tefluxed in methanol for 48 hours. Methanol was removed on a rotatory evaporator and the residue was extracted with chloroform (3×100 ml). The combined chloroform extract was filtered repeatedly (3 times) to remove potassium carbonate. Chloroform was removed from the filtrate on a rotary evaporator and the residue was taken in 50 ml 80:15:5 (v/v) acetonitrile:ethyl acetate:methanol. One equivalent of n-hexadecyl bromide (2.9 g, 9.5 mmol) was added and the mixture was refluxed for 56 hours. At this point, an additional equivalent of potassium carbonate (1.44 g, 10.5 mmol) was added and refluxing was continued for another 30 hours. Finally, one more equivalent of n-hexadecyl bromide (2.9 g, 9.5 mmol) was added and the mixture was refluxed for 24 hours. The solvent was removed on a rotary evaporator and the residue was extracted with chloroform (100 ml). Potassium carbonate was filtered from the chloroform extract and the chloroform was removed on a rotary evaporator. The residue was dissolved in ethyl acetate (30 ml) with the help of little methanol (0.3–0.5 ml) and the resulting solution of the product mixture showed three spots (with $R_f$=0.9, 0.8 and 0.7) on thin layer chromatography (TLC) using 30:70 (v/v) methanol:chloroform as the TLC developing solvent. The solution was kept at 4° C. for 36 hours. The precipitate that appeared at this point was predominantly the compound with $R_f$=0.9 which was further purified by silica gel chromatography using finer than 200 mesh size silica and eluting with 2–5% methanolic (by volume) chloroform. The NMR and HRMS of this column purified product (yield: 470 mg) showed it to be a O-n-hexadecyl derivative of the title amphiphile No 1 that did not show any gene transfection activity. The mother liquor was concentrated and dry packed with 60–120 mesh size silica. The dry packed residue was loaded on a 60–120 mesh size silica column and was eluted first with ethyl acetate and then with chloroform to wash off unreacted n-hexadecyl bromide and diethanolamine. The compounds with $R_f$=0.8 and 0.7 were then isolated as a mixture by changing the eluent to 90:10 (v/v) chloroform-:methanol. The isolated product mixture was finally dry packed with finer than 200 mesh size silica and the dry packed mixture was loaded on a finer than 200 mesh size silica column. The title amphiphiles 1 and 2 (with $R_f$=0.8 and 0.7 respectively) were finally isolated in pure forms by eluting the dry-packed column carefully with chloroform containing 2–5% methanol (by volume). The yields of the purified amphiphile 1 and amphiphile 2 were respectively 8% (500 mg, 0.787 mmol) and 12.7% (500 mg, 1.2 mmol).

$^1$H-NMR of amphiphile 1 (200 MHz, CDCl$_3$): δ/ppm=0.9 [t, 6H, C$\underline{H}_3$—(CH$_2$)$_n$—]; 1.20–1.5 [m, 52H, —(C$\underline{H}_2$)$_{13}$—]; 155–1.85 [m, 4H, (HOCH$_2$—CH$_2$)$_2$N$^+$(CH$_2$—C$\underline{H}_2$—)$_2$]; 3.4–3.6 [m, 4H, (HOCH$_2$—CH$_2$)$_2$N$^+$(C$\underline{H}_2$—CH$_2$—)$_2$]; 3.65–3.80 [m, 4H, (HOCH$_2$—C$\underline{H}_2$)$_2$N$^+$(CH$_2$—CH$_2$—)$_2$]; 4.05–4.2 [m, 4H, (HOC$\underline{H}_2$—CH$_2$)$_2$N$^+$(CH$_2$—CH$_2$—)$_2$]; 4.75–4.95(m, 2H, —O$\underline{H}$).

HRMS (FABS) m/z: Calcd (for C$_{36}$H$_{76}$NO$_2$ the 4°-ammonium ion) 554.5876 found 554.5899

$^1$H-NMR of amphiphile 2 (200 MHz,CDCl$_3$): δ/ppm=0.9 [t, 3H, C$\underline{H}_3$—(CH$_2$)$_n$—]; 1.15–1.5 [m, 26H, CH$_3$—(C$\underline{H}_2$)$_{13}$—]; 1.75–1.85 [m, 2H, (HOCH$_2$—CH$_2$)$_2$N$^+$(CH$_2$—C$\underline{H}_2$—)$_2$—]; 3.2–3.35 [m, 2H, (HOCH$_2$—CH$_2$)$_2$N$^+$(C$\underline{H}_2$—CH$_2$—)$_2$]; 3.35–3.5 [m, 4H, (HOCH$_2$—C$\underline{H}_2$)$_2$N$^+$(CH$_2$—CH$_2$—)$_2$]; 4.04.15 [m, 4H, (HOC$\underline{H}_2$—CH$_2$)$_2$N$^+$(CH$_2$—CH$_2$—)$_2$];

HRMS (FABS) m/z : Calcd (for C$_{20}$H$_{44}$NO$_2$ the 4°-ammonium ion) 330.3372 found 330.3346.

EXAMPLE 3

Procedure for preparing N-methyl-N-n-octadecyl-N-oleyl-N-hydroxyethyl-ammonium chloride (MOORAC), amphiphile No 3.

Step (a). 100 ml dry dichloromethane was cooled to 0° C. and to the cold dichloromethane solution was added 1.9 g of oleyl aldehyde (7.14 mmol), 1.92 g of stearyl amine (7.14 mmol) and 10.9 g of anhydride magnesium sulfate (7.14 mmol). The mixture was kept under stirring for 3 hours while the temperature of the stirred mixture raised gradually from 0° C. to room temperature. The magnesium sulfate was filtered from the reaction mixture and the filtrate was diluted with 50 ml of methanol. The diluted dichloromethane/methanol solution was cooled to 0° C. and to the cold solution, 0.54 g Sodium borohydride (14.0 mmol) was added. The solution was kept stirred for 4 hours during which time the temperature of the reaction mixture gradually raised to room temperature. The reaction mixture was taken in 100 ml chloroform, washed with water (2×100 ml), the chloroform layer was dried over anhydride magnesium sulfate and filtered. Chloroform was removed from the filtrate on a rotary evaporator and column chromatographic (using 60–120 mesh size silica) purification of the residue using 20–50% ethyl acetate in pet-ether as the eluent afforded 2.34 g (64% yield) of the desired intermediate secondary amine, namely, N-oley-N-n-octadecylamine.

Step (b). A mixture of 0.95 g (1.83 mmol) of N-oleyl-N-n-octadecylamine obtained in step (a) and 0.67 g (1.83 mmol) of 2-bromoethyl-tertabutyl-diphenylsilyl ether [prepared conventionally by the reaction between 2-bromoethanol and tetrabutyl-diphenylsilyl chloride in the presence of triethylamine and N,N-dimethylamino pyridine] was refluxed in ethyl acetate in presence of anhydrous potassium carbonate (0.28 g, 2.01 mmol) for 48 hours. The reaction mixture was taken in 100 ml chloroform, washed with water (2×100 ml), dried over anhydrous magnesium sulfate and filtered. Chloroform was removed from the filtrate on a rotary evaporator. Silica gel column chromatographic purification of the resulting residue using 60–120 mesh size silica and 3–4% ethyl acetate (by volume) in pet-ether as the eluent afforded 0.69 g (47% yield) of the intermediate tertiary amine, namely the O-tetrabutyldiphenylsilyl derivative of N-2-hydroxyethyl-N-oleyl-N-n-octadecylamine. The tert-butyl-diphenylsilyl protecting group of this intermediate tertiary amine (0.67 g, 0.84 mmol) was conventionally removed by stirring with tetrabutylammonium fluoride (2.1 mmol, 2.1 ml of 1M tetrabutylammonium fluoride solution in tetrahydrofuran) in dry tetrahydrofuran (cooled to 0° C.) for 4 hours during which the temperature of the reaction mixture gradually raised to room temperature. The usual work-up and silica gel column purification (as described above in detail for isolating pure protected intermediate except that the eluent used in this case was 7–10% ethyl acetate in pet-ether) of the product mixture afforded 0.32 g (67.5% yield) of pure deprotected tertiary amine namely, N-oley-N-n-octadecyl-N-2-hydroxyethylamine.

Step (c). Quaternization of 0.12 g (0.21 mmol) of N-oleyl-N-n-octadecyl-N-2-hydroxyethylamine obtained in step (b) was carried out in 5 ml of 5:4 chloroform methanol (v/v) at room temperature for overnight using huge excess of methyl iodide (4 ml). The solvents were removed on a rotary evaporator and silica gel column chromatographic purification of the residue using 60–120 mesh size silica and 3–4% methanol (by volume) in chloroform afforded the quaternary iodide salt of the title A amphiphile. Finally, 0.08 g of pure title amphiphile No. 3 in 91.9% yield was obtained by subjecting the quaternized ammonium iodide salt (0.1 g, 0.14 mmol) to repeated (4 times) chloride ion-exchange chromatography, each time using a freshly generated Amberlyst A-26 chloride ion exchange column column and about 80 ml of chloroform as the eluent. All the isolated intermediates gave spectroscopic data in agreement with their assigned structures shown in FIG. 4. Thus, the title amphiphile 3 was prepared in 3 steps with an overall yield of 18.7%.

$^1$H-NMR of amphiphile 3 (200 MHz, CDCl$_3$): $\delta$/ppm= 0.89 [t, 6H, C$\underline{H}_3$—(CH$_2$)$_n$—]; 1.20–1.45 [m, 52H, —(CH$_2$)$_{13}$—]; 1.60–1.80 [(br, 4H, CH$_3$(HOCH$_2$—CH$_2$)N$^+$(CH$_2$—C$\underline{H}_2$—)$_2$]; 1.90–2.10 (m, 4H, —C$\underline{H}_2$—CH=CH—CH$_2$—); 3.35 [s, 3H, C$\underline{H}_3$(HOCH$_2$—CH$_2$)N$^+$(CH$_2$—CH$_2$—)$_2$)]; 3.41–3.58 [br, 4H, CH$_3$(HOCH$_2$—CH$_2$)N$^+$(C$\underline{H}_2$—CH$_2$—)$_2$]; 3.65–3.80 [br, 2H, CH$_3$(HOCH$_2$—CH$_2$)N$^+$(CH$_2$—CH$_2$—)$_2$]; 4.07–4.12 [br, 2H, CH$_3$(HOC$\underline{H}_2$—CH$_2$)N$^+$(CH$_2$—CH$_2$—)$_2$]; 5.32 (m, 2H, —CH$_2$—CH=C$\underline{H}$—CH$_2$—).

HRMS (FABS) m/z : Calcd (for C$_{39}$H$_{80}$NO, the 4°-ammonium ion) 578.6239, found 578.6233.

EXAMPLE 4

Procedure for preparing N,N,-di[O-hexadecanoyl]hydroxyethyl-N-hydroxyethyl-N methylammonium bromide (DOHEMAB), amphiphile 5.

Step (a). Di-O-palmitoylation of N-methyl-diethanolamine was effected following a published protocol [Tundo et al. *J. Am. Chem. Soc.* 104, 456–461]. Briefly, N-methyl-diethanolamine (1 g, 8.39 mmol) was reacted with palmitoyl chloride (5.075 g, 18.5 mmol) in 10 ml dry N,N-dimethylformamide at 0° C. and the temperature was gradually raised to room temperature within a period of 4 hours. The resulting hydrochloride salt of N-methyl-di-O-palmitoylethanolamine was filtered, crystallized from 20 ml of dry ether. Finally, recrystallization from 20 ml 5:15 (v/v) methanol:ethyl acetate afforded 3.8 g of the pure hydrochloride intermediate in 68% yield.

Step (b). The recrystallized hydrochloride salt (200 mg) was stirred for 5 minutes in a dichloromethane (10 ml)/1.0 M aqueous NaOH (10 ml) biphasic system. The top aqueous layer was discarded and the lower organic layer was washed with water (2×50 ml), dried over anhydrous sodium sulfate, filtered and dichloromethane was removed on a rotary evaporator. Pure N-methyl-di-O-palmitoylethanolamine (0.14 g, 0.22 mmol, 74.1% yield) was purified from the residue by silica gel column chromatography using 60–120 mesh size silica and 98:2 (v/v) chloroform:methanol as the eluent.

Step (c). Quaternization of N-methyl-di-O-palmitoylethanolamine was effected by reacting the purified tertiary amine (0.14 g, 0.22 mmol) with 1.5 equivalent of neat 2-bromoethanol (0.063 g, 0.34 mmol) at 85° C. for 4 hours. The quaternized title amphiphile salt 5 was crystallized from the residue using 10 ml 2:8 (v/v) benzene:n-pentane. Silica gel column chromatographic purification of the resulting crystal using 60–120 mesh size silica and 4:96 (v/v) methanol:chloroform as the eluent finally afforded 0.04 g of the pure title amphiphile 5 in 16.5% yield. All the isolated intermediates gave spectroscopic data in agreement with their assigned structures. Thus, the title amphiphile 5 was prepared in 3 steps with an overall yield of 8.3%

$^1$H-NMR of amphiphile 5 (200 MHz, CDCl$_3$): $\delta$/ppm= 0.88 [t, 6H, C$\underline{H}_3$—CH$_2$—C$_{13}$H$_{26}$—]; 1.20–1.40 [m, 48H, —(C$\underline{H}_2$)$_n$—]; 1.50–1.68 [m, 4H, CH$_3$(HOCH$_2$—CH$_2$)N$^+$(CH$_2$—CH$_2$—O—CO—C$\underline{H}_2$—CH$_2$—)$_2$]; 2.21–2.40 [2t, 4H, CH$_3$(HOCH$_2$13 CH$_2$)N$^+$(CH$_2$—CH$_2$—O—CO—C$\underline{H}_2$—CH$_2$—)$_2$]; 3.43 [s, 3H, C$\underline{H}_3$(HOCH$_2$—CH$_2$—CH$_2$—O—CO—CH$_2$—CH$_2$—)$_2$]; 3.50–4.30 [m, 9H, CH$_3$(H$\underline{O}$CH$_2$—C$\underline{H}_2$)N$^+$(C$\underline{H}_2$—CH$_2$—O—CO—CH$_2$—CH$_2$—)$_2$]; 4.51–4.58 [br, t, 4H, CH$_3$(HOCH$_2$—CH$_2$)N$^+$(CH$_2$—C$\underline{H}_2$—O—CO—CH$_2$—CH$_2$—)$_2$].

HRMS (FABS) m/z: Calcd (for C$_{39}$H$_{79}$NO$_5$, the 4°-ammonium ion) 641.5958, found 641.5907.

What is claimed is:

1. A process for the synthesis of novel cationic amphiphiles that facilitate intracellular delivery of biologically active molecules, said amphiphiles represented by the following structural formula (I):

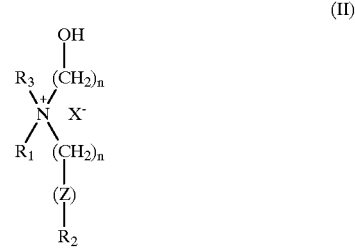

(II)

wherein:
n is an integer between 1 and 3;
R$_1$ independently, represents either a saturated aliphatic group or an unsaturated aliphatic group (from C$_8$ to C$_{20}$);
Z represents a methylene (—CH$_2$—) group;
R$_2$, independently, represents a long-chain saturated alkyl group (from C$_7$ to C$_{19}$);
R$_3$ is a small allyl group (from C$_1$ to C$_3$);
X is either a halogen atom or a tosylate group,
said process comprising the steps of:
  (a) coupling an appropriate aliphatic saturated or unsaturated aldehyde with an alkyl amine followed by the reduction of the resulting imine to obtain the corresponding secondary amine;
  (b) reacting the secondary amine obtained in step (a) with the appropriate hydroxyl-protected hydroxyalkyl halide followed by removal of the hydroxyl protecting group to obtain the corresponding N-hydroxyalkyl group containing tertiary amine, and (c) quaternizing the resulting N-hydroxyalkyl group containing tertiary amine obtained in step (b) with the appropriate alkyl halide or alkyl tosylates in a mixed polar solvent.

2. A process as claimed in claim 1 wherein the saturated or unsaturated aldehyde used is oleyl aldehyde.

3. A process as claimed in claim 1 wherein the alkyl amine used is n-octadecyl amine.

4. A process as claimed in claim 1 wherein the tertiary amine is quarternised with methyl iodide.

5. A process as claimed in claim 1 wherein the mixed polar solvent in step (c) comprises a mixture of methanol and chloroform.

6. A process as claimed in claim 1 wherein the resultant tertiary amine of step (b) is N-hydroxyethyl-N-oleyl-N-n-octadecyl-amine.

7. A process as claimed in claim 1 wherein the reaction of amine with aldehyde is performed in dichloromethane.

8. A process as claimed in claim 1 wherein the reaction is carried out at a temperature ranging between −78° C. to 10° C.

9. A process as claimed in claim 1 wherein the reaction is followed by the reduction of the resulting imine with sodium borohydride in a mixed polar solvent at a temperature in the range of −5° C. to 40 ° C.

10. A process as claimed in claim 1 wherein the reaction of step (b) is carried out in the polar solvent to obtain tertiary intermediate.

11. A process disclaimed in claim 1 wherein the polar solvent is selected from from the group of ethyl acetate, N,N methylformamide, and acetonitrile.

12. A process as claimed in claim 1, wherein the reaction is carried out in the presence of weak base selected from sodium carbonate and potassium carbonate.

13. A process as claimed in claim 1 wherein the solvent used in step (b) for the removal of hydroxyl protecting group is selected from the group consisting of tetrahydrofuran and dimethyl formamide.

14. A process as claimed in claim 1 wherein quarternization in step (c) is carried out at a temperature ranging between −5° C. to 40° C.

* * * * *

UNITED STATES PATENT AND TRADEMARK OFFICE
CERTIFICATE OF CORRECTION

PATENT NO.   : 6,333,433 B1
DATED        : December 25, 2001
INVENTOR(S)  : Rajkumar Banerjee et al.

It is certified that error appears in the above-identified patent and that said Letters Patent is hereby corrected as shown below:

<u>Title page,</u>
Item [54], "N-HYDROXYALKL" should read -- N-HYDROXYALKYL--.

<u>Column 16,</u>
Line 58, "allyl" should read -- alkyl --

<u>Column 18,</u>
Line 1, "A process as disclaimed" should read -- A process as claimed --.
Lines 10 and 11, "N,N methylformamide" should read -- N,N-dimethylformamide --.

Signed and Sealed this

Tenth Day of September, 2002

Attest:

JAMES E. ROGAN
*Attesting Officer*   *Director of the United States Patent and Trademark Office*